US006936003B2

(12) United States Patent
Iddan

(10) Patent No.: US 6,936,003 B2
(45) Date of Patent: Aug. 30, 2005

(54) IN-VIVO EXTENDABLE ELEMENT DEVICE AND SYSTEM, AND METHOD OF USE

(75) Inventor: Gavriel J. Iddan, Haifa (IL)

(73) Assignee: Given Imaging LTD, Yoqneam Ilite (IL)

( * ) Notice: Subject to any disclaimer, the term of this patent is extended or adjusted under 35 U.S.C. 154(b) by 0 days.

(21) Appl. No.: 10/694,092

(22) Filed: Oct. 28, 2003

(65) Prior Publication Data

US 2004/0176664 A1 Sep. 9, 2004

Related U.S. Application Data

(60) Provisional application No. 60/421,788, filed on Oct. 29, 2002.

(51) Int. Cl.[7] .................................................. A61B 1/04
(52) U.S. Cl. ....................... 600/114; 600/109; 600/118; 600/101; 600/115; 600/117; 600/160
(58) Field of Search .......................... 600/109, 114–115, 600/117–118, 160

(56) References Cited

U.S. PATENT DOCUMENTS

| | | | |
|---|---|---|---|
| 3,971,362 A | 7/1976 | Pope et al. | |
| 4,278,077 A | 7/1981 | Mizumoto | |
| 4,689,621 A | 8/1987 | Kleinberg | |
| 4,844,076 A | 7/1989 | Lesho et al. | |
| 5,279,607 A | 1/1994 | Schentag et al. | |
| 5,604,531 A | 2/1997 | Iddan et al. | |
| 5,662,587 A | * 9/1997 | Grundfest et al. | 600/114 |
| 5,819,736 A | 10/1998 | Avny et al. | |
| 6,162,171 A | * 12/2000 | Ng et al. | 600/141 |
| 6,240,312 B1 | 5/2001 | Alfano et al. | |
| 6,402,686 B1 | * 6/2002 | Ouchi | 600/139 |
| 6,719,684 B2 | * 4/2004 | Kim et al. | 600/101 |
| 2001/0051766 A1 | 12/2001 | Gazdzinski | |
| 2002/0198439 A1 | 12/2002 | Mizuno | |
| 2003/0013370 A1 | 1/2003 | Glukhovsky | |
| 2003/0069474 A1 | 4/2003 | Couvillon, Jr. | |

FOREIGN PATENT DOCUMENTS

| | | |
|---|---|---|
| DE | 34 40 177 | 5/1986 |
| JP | 4109927 | 4/1992 |
| JP | 5015515 | 1/1993 |
| JP | 2001224553 | 8/2001 |
| WO | WO 98/11816 | 3/1998 |
| WO | WO 01/08548 | 2/2001 |
| WO | WO 01/50941 | 7/2001 |
| WO | WO 01/65995 | 9/2001 |
| WO | WO 01/87377 | 11/2001 |
| WO | WO 02/26103 | 4/2002 |

OTHER PUBLICATIONS

"www.rfnorkia.com"—NORIKA3, Dec. 24, 2001.
"Wireless transmission of a color television moving image from the stomach using a miniature CCD camera, light source and microwave transmitter". Swain CP, Gong F, Mills TN. Gastrointest Endosc 1997;45:AB40.
"BBC News Online—Pill camera to 'broadcast from the gut'", Feb. 21, 2000, www.news.bbc.co.uk.
"Electroactive Polymer Actuators as Artificial Muscles", Y. Bar–Cohen, Ed., Spie Press, 2001.
"The 'Elephant Trunk' Manipulator, Design and Implementation", M.W. Hannan and I.D. Walker.
"Robots for the future"—Shin–ichi, et al., Nov. 29, 2001.
"The Radio Pill", Rowlands, et al., British Communications and Electronics, Aug. 1960, pp. 598–601.
"Video Camera to "TAKE""—RF System lab, Dec. 25, 2001.
"Wellesley company sends body montiors into space"—Crum, Apr. 1998.

* cited by examiner

Primary Examiner—Beverly M. Flanagan
Assistant Examiner—Matthew Kasztejna
(74) Attorney, Agent, or Firm—Pearl Cohen Zedek Laizer LLP

(57) ABSTRACT

An in-vivo device, such as an autonomous imager or other suitable in-vivo device, includes a moveable arm, extendible element, or proboscis. The in-vivo device may include sensors, such as imagers, etc. The device may transmit sensing information via, for example, wireless transmission, or wired transmission.

26 Claims, 7 Drawing Sheets

IN-VIVO EXTENDABLE ELEMENT DEVICE AND SYSTEM, AND METHOD OF USE

RELATED APPLICATION DATA

The present application claims benefit from prior U.S. Provisional Patent Application Ser. No. 60/421,788 filed on 29 Oct. 2002 and entitled "IN-VIVO EXTENDABLE ELEMENT DEVICE AND SYSTEM, AND METHOD OF USE", incorporated by reference herein in its entirety.

FIELD OF THE INVENTION

The present invention relates to the field of in vivo diagnosis and therapeutics, more specifically, the present invention relates to a system and a device for in vivo diagnosis and therapeutics including an extendable and/or moveable element.

BACKGROUND

Devices and methods for performing in-vivo medical procedures and imagery are known in the art. Such devices may be, for example, inserted into a patient's body and advanced through internal lumens or cavities of the body to a site of interest located inside a patient's body.

One group of in-vivo medical devices includes various endoscopic systems. The imaging capabilities of such endoscopic systems may be limited and provide only a partial forward field of vision, although some endoscope systems do allow for the field of view to be changed. Additionally, although a variety of medical instruments may be passed through the endoscopic tube to enable treatment at a site of interest, such instruments are usually relatively cumbersome and may require complicated controls and cause pain or discomfort to a patient.

Another group of devices for performing in-vivo medical procedures and imagery includes autonomous in-vivo devices. An example of such devices may be a swallowable device such as a capsule having an optical assembly capable of providing images from inside a body cavity or lumen such as the gastrointestinal (GI) tract. The design of autonomous in-vivo devices, such as swallowable capsules, may be subjected to size constraints and other limitations.

It would be desirable to have a medical instrument having improved qualities such as maneuverability and control and substantially small dimensions that is suitable for a wide variety of medical tasks, and that in addition may include controls or devices for manipulating objects, tools or substances within or external to the device.

SUMMARY OF THE INVENTION

There is thus provided, according to an embodiment of the present invention, a typically in vivo system and/or device including one or more extendable and/or moveable elements or arms, which may be termed proboscises. The proboscises may, for example, act as one or more "arms" to perform a variety of tasks or, for example, may be used to propel, move, stabilize or hold the device. In some embodiments, the arms or proboscises may be progressively extendable, and the extension of the proboscis may be omni-directionally controlled by, for example, outside direction by an operator, or autonomously. In another embodiment of the present invention, an autonomous in vivo device may include one or more proboscises. In alternate embodiments, the extendable element may be used in a non-medical field or application. The device may be autonomous, and may include an on-board power supply, such as a battery or a power receiving system.

Various suitable structures for an arm or extendible element may be used. For example, in one embodiment, a plurality of segments may be used. A set of control wires may connect to the arm or element, and if segments are used may connect to individual segments. Devices that may be used to move the arm or element may include, for example, piezo material, shape memory material, motors, or other suitable elements.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

Figure 1A:
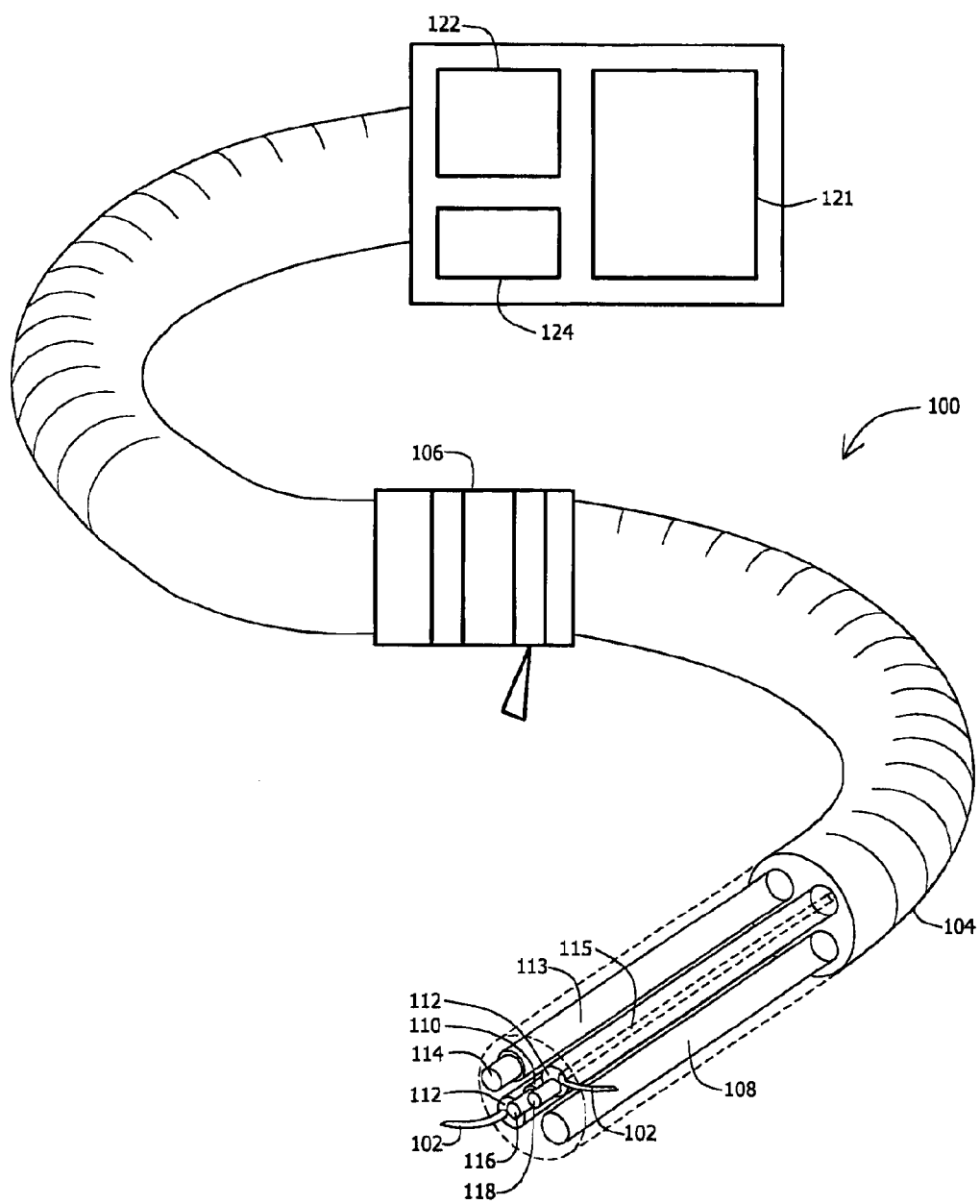
FIG. 1A is a block diagram illustration of an in vivo system, according to an embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However it will be understood by those of ordinary skill in the art that the present invention may be practiced without these specific details. In other instances, well-known methods and procedures have not been described in detail so as not to obscure the present invention.

Throughout the specification the term "in-vivo procedures" may relate to any diagnostic and/or therapeutic procedures performed inside the human body, for example, but not limited to, procedures of gastroenterology, procedures within or on blood vessels, procedures of gynecology and laparoscopic surgery procedures.

Embodiments of the present invention relate to an in-vivo system and device-including one or more extendable elements or arms, which may be termed proboscises. In alternate embodiments, the extendable element may be used in a non-medical field or application.

The arm or proboscis may be, for example, progressively extendable. The extension of the proboscis may be, for example, omni-directionally controlled.

In another embodiment of the present invention, an autonomous in-vivo device may include one or more proboscises.

Reference is made now to FIG. 1A, which is an illustration of an in-vivo system according to an embodiment of the present invention. The system 100 may include one or more extendable arms, elements or proboscises 102, a tube 104 such as an endoscopic tube, and, for example, a handpiece 106. Each of the one or more extendable proboscises 102 are typically located at the distal portion of the endoscopic tube 104, but in alternate embodiments may be located at other portions, such as a mid-portion.

Units such as an illumination source 114, one or more in-vivo medical instruments 118, and one or more sensors such as image sensor 116 may also be located at the distal portion of the tube 104. Other sensors, such as pH sensors, pressure sensors, etc., may be used. The illumination source 114 (e.g. one or more LEDs) may be adapted to, for example, illuminate an area inside the patient's body. The image sensor 116 (e.g. a CMOS image sensor; other suitable sensors may be used) may be adapted to collect reflected light. In some embodiments, the illumination source 114 may be configured to output, and the image sensor 116 may be configured to collect, electromagnetic radiation. The instruments 118 may be suitable in-vivo medical instruments, such as graspers, blades, clamps, tissue collecting baskets, means for delivering treatment at a specific location, stents, catheters, suturing devices, forceps, dilatation balloons, and others. The sensors may also be suitable sensors, including but not limited to a temperature sensor, a pH meter, a biochemical analyte assay or identifier, a sensor for determining electrical impedance of tissues, an optical sensor, such as a spectrometer and other sensors. The system 100 may include other components or arrangements of components. For example, in some embodiments, an imaging system may be omitted.

In some embodiments, an imaging unit placed on the tube 104 may transmit images wirelessly. For example, the imaging unit and its use, and a reception and display system which may be used with the imaging unit, are similar to embodiments disclosed in U.S. Pat. No. 5,604,531 to Iddan et al. and/or WO 01/65995 entitled "A Device And System For In Vivo Imaging", published on 13 Sep. 2001, both of which are hereby incorporated by reference. In other embodiments, other imaging units, receivers and processing units may be used.

In one embodiment, the proboscis is approximately 1 mm in diameter and 15–20 mm in length, but other dimensions may be used. According to some embodiments of the present invention, each of the one or more extendable proboscises 102 may be designed to mimic or include one or more functions of suitable in vivo medical instrument, sensor or imager, including but not limited to graspers, blades, clamps, collecting baskets or containers for tissue or fluid (which may include particles), scalpels, stents, catheters, suturing devices, forceps, dilatation balloons, injectors, forceps, anchors, drug applicators, samplers, biopsy samplers, an electrode or electrodes, suction tubes, temperature sensors, optical sensors, pH meters, and others. Accordingly, the proboscis 102 may be adapted to perform, or may include components allowing it to perform a wide variety of functions. For example, the extendable proboscis 102 may be adapted to perform tissue cutting, tissue welding, suturing, cauterizing, ablating, clamping, biopsy and tissue sampling, optical sensing, chemical sensing, application of substance, injection of substances, imaging, and temperature sensing, etc. However it should be noted that the extendable proboscis 102 of an embodiment of the present invention may not be limited to such functions or procedures, and that the extendable proboscis 102 of an embodiment of the present invention may be designed to perform a wide variety of in vivo functions or procedures, or to carry or deliver components capable of performing such functions or procedures. For example, an extendable proboscis 102 according to an embodiment of the present invention may include an attachment point allowing a, for example, a blade to be attached and manipulated.

The proboscis 102 may, for example, be folded or coiled when in an inactive mode, and possibly contained within a storage section or cavity, and may be unfolded when in an extended mode. According to one embodiment of the present invention the extendable proboscis 102 may be coiled around itself when in inactive mode and may be partly or fully uncoiled when in extended mode. According to a further embodiment of the present invention the extension of the proboscis 102 may be controlled, such that only a selected portion of the extendable proboscis 102 may be unfolded or alternatively, the extendable proboscis 102 may be completely unfolded. The control of the extendable proboscis 102 is discussed in greater detail herein.

The tube 104 may be designed and fabricated similarly to known catheters, endoscopes, needles, stents, laparascopes, rigid endoscopes and the like, in accordance with specific requirements. For example, the tube 104 may include a water/air channel or channels 108, a working channel 110, for passing instruments and tools, a control channel 112 (which may include, for example, one or more control wires 115) for passing control wires and conductive wires, and an illumination channel 113 for passing illumination fibers through the tube 104. Other components and arrangements of components may be used. The control wires 115 and the conductive wires passing through the control channel 112 may be operatively connected to one or more of the proboscises 102, illumination source 114, imaging sensor 116, instruments 118 and other sensors. The control wires may be adapted to pass control signals to one or more of the proboscises 102, illumination source 114, imaging sensor 116, instruments 118 and other sensors. The conductive wires may be adapted to energize one or more of the proboscises 102, illumination source 114, imaging sensor 116, instruments 118 and other sensors. Each one of the channels 110, 112 and 113 passing through the tube 104 may extend from the proximal end of the tube 104 throughout the length of the tube 104 to the distal end of the tube 104, or, alternately, may extend part way, if appropriate. It may thus be possible to externally remotely control and energize one or more of the proboscises 102, illumination source 114, imaging sensor 116, instruments 118 and other sensors, located inside the patient's body. In addition, it may be possible to deliver illumination through the illumination fibers passing through the illumination channel 113 to an area of interest inside the patient's body and also to flush or insufflate an area inside the patient's body by flowing air or water through the air/water channel or channels 108.

The handpiece 106 may be operatively connected to the proximal tip of the endoscopic tube 104, and possibly, to each one of the channels, wires, fibers or the like, passing therethrough. The handpiece 106 may thus be adapted to control one or more of the proboscises 102, illumination source 114, imaging sensor 116, instruments 118 and other sensors, specifically, but not exclusively, when located inside the patient's body. The handpiece 106 may also be adapted to control the air/water supply to the air/water channel 108, and the delivery of electromagnetic radiation to the illumination fibers. The handpiece 106 may include buttons, levers, pulleys or the like for controlling or regulating one or more aspects of the operation of one or more of the elements of the in-vivo medical system 100.

The in-vivo medical system 100 may further include, for example, a display unit 121, a processor 122 and controller 124. Controller 124 may be, for example, a microcontroller, microprocessor, computer on a chip, or a computer such as a personal computer or workstation operating software. The display unit 121 may receive image data or image signals, or other data, from the image sensor 116 or from other sensors included within system 100 (e.g., temperature, pressure) and may be adapted to, for example, display an image or series of images corresponding to the image data or signals. The processor 122 may receive data from one or more sensors 116 and may be adapted to process the data. The processed data may be input to the display unit 121 for display. In addition or in alternative, the processed data may also be input to the controller 124.

The controller 124 may be operatively connected to one or more of the proboscis 102, illumination source 114, imaging sensor 116, instruments 118 or other sensors. The controller 124 may be adapted to generate control signals (e.g. operation parameters), possibly, in accordance with the input processed data, for controlling one or more aspects of the operation of one or more of the proboscis 102, illumination source 114, imaging sensor 116, instruments 118 or other sensors. The controller 124 (and/or other suitable components, such as another suitable controller, receiver, transceiver, etc) may react to external operator control, e.g., a human using, for example, a joystick; in such case the controller 124 translates data input from the joystick to control signals which are sent to the proboscis 102 via, for example, control wire(s) 115. The controller may react to sensor information and alter the proboscis 102 position accordingly. In one embodiment control signals are those such as up/down and left/right, as described herein.

The controller 124 may be operated in conjunction with the handpiece 106. For example, the controller 124 and the handpiece 106 may be adapted to control different aspects, instruments or functions of the in-vivo medical system 100. However, in accordance with other embodiments of the present invention, the controller 124 and the handpiece 106 may be adapted to control some of the same aspects, instruments or functions of the in-vivo medical system 100 and a set of priorities and overrides may be implemented.

Figure 1B:
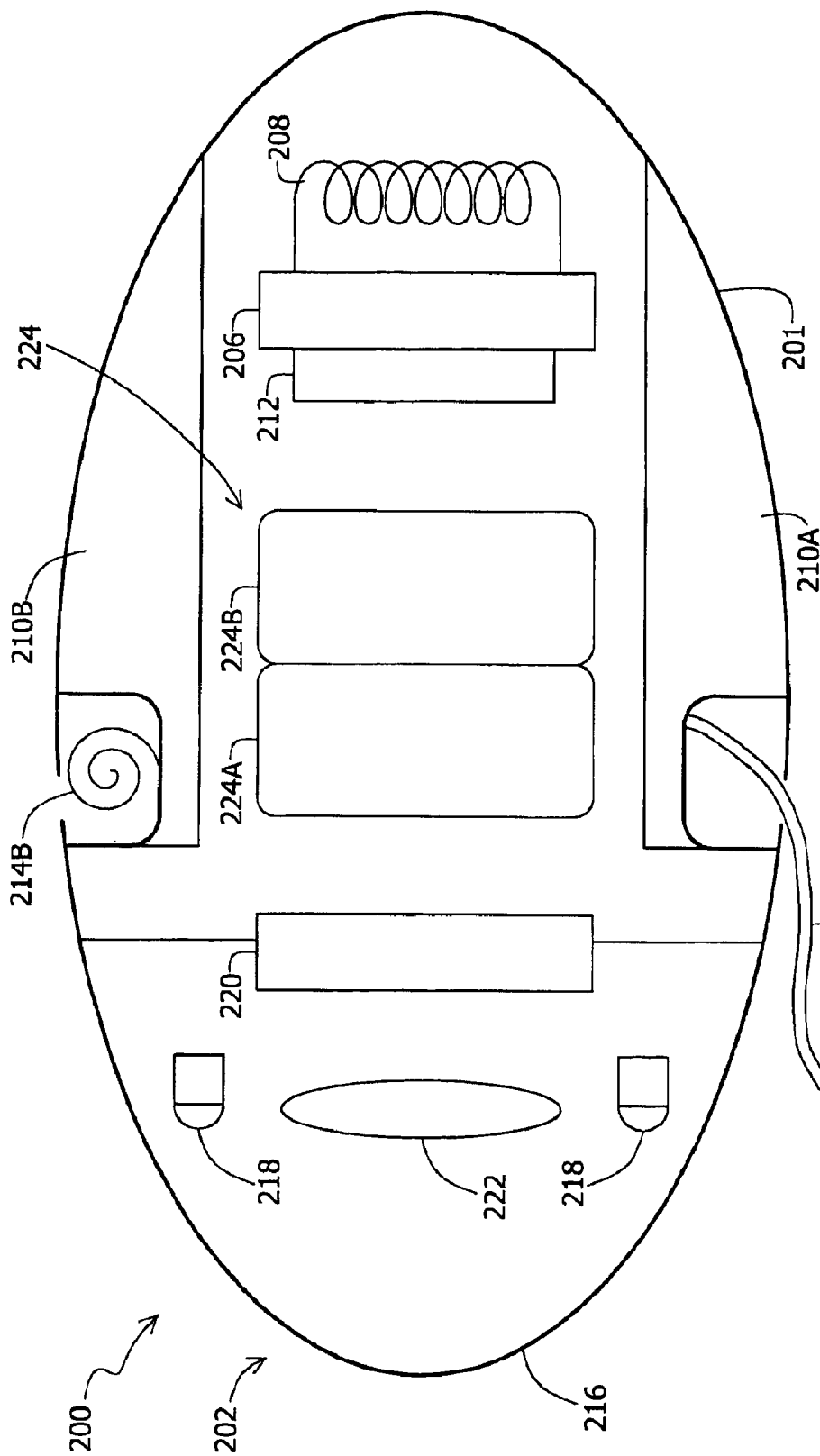
FIG. 1B is a block diagram illustration of an autonomous in vivo device, according to another embodiment of the present invention.

Reference is made now to FIG. 1B, which is a schematic illustration of an in vivo device, according to an embodiment of the present invention. In vivo device 200 is typically autonomous and is typically self contained, but need not be. For example, the device may be a capsule or other unit where all the components are substantially contained within a container or shell, and where the device does not require any wires or cables to, for example, receive power or transmit information. The device may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source. In some embodiments, the in-vivo device and its use, and a reception and display system which may be used with the device, are similar to embodiments disclosed in U.S. Pat. No. 5,604,531 to Iddan et al. and/or International Application publication number WO 01/65995 entitled "A Device And System For In Vivo Imaging", published on 13 Sep. 2001, each incorporated by reference in its entirety. The system and method of an embodiment of the present invention may be used with other suitable autonomous in-vivo systems, and other suitable reception and display systems, having different structures and different methods of operation.

The autonomous in-vivo device 200 may include one a container or housing 201. Within the housing 201, may be, for example, an optical assembly 202, a power assembly 224, a transceiver 206, one or more antenna(s) 208, one or more storage tanks 210A and 210B, a controller 212 and one or more extendable elements or proboscises 214A and 214B. However, some of the above elements or assemblies may be located partially or completely externally to the housing 201.

The optical assembly 202 may include, for example, an optical dome 216. The optical dome 216 may be part of the housing 201. The device 200 may include one or more illumination sources 218 (e.g. white light LED, monochromatic light or any suitable combination thereof, or other suitable illumination sources), one or more solid state imagers 220, such as a CMOS image sensor or a CCD, and one or more optical elements 222, such as focusing lenses and mirrors. The optical dome 216 may be transparent to wavelengths used for imaging by the imager 220. The one or more illumination sources 218 may be adapted to illuminate a selected area. In some embodiments, the illumination sources 218 may be adapted to produce electromagnetic radiation having specific spectra. Filters (not shown) may be used in conjunction with one or more of the illumination sources 218 to produce light having specific spectra. Optionally, at least a portion of the electromagnetic radiation may be manipulated by the optical elements 222, prior to exiting the dome 216. A portion of the electromagnetic radiation may be reflected back through the optical dome 216, possibly from an area inside the patient's body. At least a portion of the reflected electromagnetic radiation may be received by the solid state imager 220. Optionally, the reflected electromagnetic radiation may be manipulated by the optical elements 222, prior to being received by the solid state imager 220. In alternate embodiments, the system and method of an embodiment of the present invention may be used with an autonomous capsule without an imager.

The power assembly 224 may include one or more batteries 224A and 224B. Batteries 224A and 224B may include, for example, silver oxide batteries, lithium batteries, or other electrochemical cells having a high energy density, rechargeable batteries, or the like, but may include other suitable elements. The batteries 224A and 224B may be operatively connected to one or more of the elements of the in-vivo device 200, such that the batteries 224A and 224B may be adapted to energize one or more of these elements. For example, the power assembly 224 may be operatively connected to one or more of the illumination sources 218, the solid state imager 220, the proboscis 214A and 214B, the storage tanks 210A and 210B, the controller 212, the transceiver 206 and/or the antenna(s) 208. According to some embodiments of the present invention, an internal power source may be a device to receive power induced from an external source. For example, power assembly 224 may include a suitable power receiving unit, for receiving power from an external source. The power may be induced, for example, in the form of radio waves or magnetic waves, from a source located outside the patient's body (not shown) and a converter located within the housing 201, for example part of power assembly 224, may he adapted receive the waves, convert them to energy and supply the energy to each of the one or more elements located inside the housing 201. The converter may be adapted to convert the energy to a suitable form, including but not limited to, electricity, magnetic field, electromagnetic radiation, chemical potential, or the like. According to another embodiment of the present invention, the housing 201 may be connected to an external energy source (not shown) using one or more wires (not shown). The wires may be operatively connected to the housing 201 at one end, and to the external energy source at the other end. Alternatively, the wires may be operatively connected directly to each of the one or more elements of interest, located inside the housing 201. It may thus be possible to power one or more of the elements located inside the housing 201 using an external power source.

Transceiver 206 may operate using, for example, radio waves, ultrasonic transmission, or other suitable transmission methods. The transceiver 206 may include one or more receivers and one or more transmitters. The transceiver 206 may be a receiver or may be a transmitter, or if suitable, both. Alternatively, the receivers and transmitters may be combined in a single transceiver element or a transceiver array. In an embodiment where the input of data is not required, the transceiver 206 may be a one-way transmitter.

Control of the device 200, including control of the proboscis 214A and 214B, may be similar to that described above, with FIG. 1A. The transceiver 206 may be operatively connected to one or more antenna(s) 208, which may include an antenna array. The transceiver 206 together with the antenna(s) 208 may be adapted to receive incoming communications from outside the body (e g., control signals or movement signals), and to transmit outgoing communications from inside the housing 201 to a destination located outside the patient's body. Typically, such transmissions are performed using radio waves, although other transmission methods are possible. For example, wired transmission may be used. The controller 212 may be operatively connected to the transceiver 206 and to one or more of the proboscises 214A and 214B, illumination source 218, solid state imagers 220, optical elements 222, batteries 224A and 224B, antenna (s) 208 or any other elements within the housing 201.

The controller 212 may include a processor (not shown), such as a microcontroller or a computer on a chip. The processor may input inbound signals received by the transceiver 206 and may process the inbound signal. The inbound signals may be, for example, control signals generated by a user externally, for controlling one or more aspects of the operation of the autonomous in-vivo device 200. Typically, the autonomous in-vivo device 200 may be suitable for a single use. The processor may also receive outbound signals (e.g. image signals from the solid state imager 220, power level of the batteries 224A and 224B, treatment parameters obtained by the proboscis 214A and 214B, etc.), process the outbound signals and output the processed outbound signal to the transceiver 206 for transmission outside of the patient's body. In alternate embodiments, different components or sets of components may be used. For example, the controller 212 may be part of, combined with, or integrated within the transceiver 206 or a transmitter. Controller 212 may, for examples, send movement signals or control signals to an arm or extendible element such as proboscis 214.

In one embodiment, for each proboscis 214, control signals such as up/down and left/right, or up/down for each segment and left/right for each segment, or other signals, are received by transceiver 206, possibly modified (e.g., amplified, processed to be more suitable for the proboscis), and sent to the proboscis 214. Other control signals, such as to operate a tool, open a valve on a tank, inject, etc., may be included and sent to the proboscis 214 or appropriate section of the proboscis. Such control signals may be supervised and initiated by an external operator reacting to signals-sent from the device 200; for example video signals. The control signals sent from an external source may be based on, for example, a mathematical model of the proboscis dynamics which may help in generating the proper commands. Alternately, such control signals may be modified by, for example, controller 212 or transceiver 206 based on such models.

The extendable proboscises 214A and 214B may be housed within the housing 201 when in retracted mode (e.g. 214B), and may extend out of the housing 201 when in extended (e.g. 214A) or partially extended mode. Optionally, when in retracted mode, the proboscises 214A and 214B may be coiled around themselves. In some embodiments, arms or extendible elements such as proboscises 214A and 214B need not be retracted within a housing, or retracted or folded (e.g., retracted or folded against a housing) at any point. For example, a device 200 may be inserted (e.g., ingested) with arms, extendable elements, or proboscises partially or completely extended.

According to some embodiments of the present invention, the proboscises 214A and 214B may be designed to functionally mimic or to carry or move suitable in-vivo medical instruments, sensors or imagers, including but not limited to graspers, blades, clamps, tissue collecting baskets, scalpels, stents, catheters, suturing devices, forceps, dilatation balloons, injectors, forceps, anchors, drug applicators, samplers, biopsy samplers, an electrode or electrodes, suction tubes, temperature sensors, optical sensors, pH meters, and others. Accordingly, the proboscises 214A and 214B may be adapted to perform any one or more of a wide variety of functions. For example, the extendable proboscises 214A and 214B may be adapted to perform any of the following functions or procedures: tissue cutting, tissue welding, suturing, cauterizing, ablating, clamping, biopsy and tissue sampling, optical sensing, chemical sensing, application of substance, injection of substances, imaging, and temperature sensing. However, it should be noted that the extendable proboscis 214A and 214B of an embodiment of the present invention may not be limited to such functions or procedures, and that the extendable proboscises 214A and 214B of an embodiment of the present invention may be designed to perform a wide variety of in vivo functions or procedures. Not necessarily all of these functions and procedures and the corresponding designs will be discussed herein. Proboscises 214A and 214B may also perform functions such as moving or propelling the device 200, or holding the device 200 in one place.

The device 200 may include, for example, one or more storage tanks 210A and 210B. The extendable elements or proboscises 214A and 214B may be operatively connected to, or may be able to manipulate storage tanks 210A and 210B or substances within storage tanks 210A and 210B. The storage tanks 210A and 210B maybe adapted to store substances, liquids or gasses (e.g adhesive substances, medication, water, in-vivo samples, etc.) to be applied to area inside a patient's body or collected from a patient. The substances, liquids or gasses stored in the storage tanks 210A and 210B may be applied to or onto an area inside the patient's body, for example through or by the proboscis 214A and 214B which may be suitably configured with a channel or tube, or may be attached to or move a channel, tube, hose or lumen. The storage tanks 210A and 210B may also be adapted to store samples collected from within the patient's body (e.g. gas samples, blood samples, tissue samples, etc.) For example, one or more of the proboscis 214A and 214B may be adapted to collected gas samples, blood samples, tissue samples, or the like and the samples may be transferred to one or more of the storage tanks 210A and 210B, for storage In such case, the proboscis 214A and 214B may be hollow, or may include a lumen, vias or tubes internally or externally. For example, a pump 270 (FIG. 1C) may be used to provide suction and transfer materials to a tank and lumen 310 (FIGS. 2A and 2B) may transport materials. According to an embodiment of the present invention, the stored samples may be analyzed within the housing 201 and the analyzed data may be transmitted outside the patient's body. The stored samples may also be retrieved and taken for analysis outside the patient's body. In an alternate embodiment, a lumen or channel need not be included, and the extendable elements may be substantially solid.

Figure 1C:
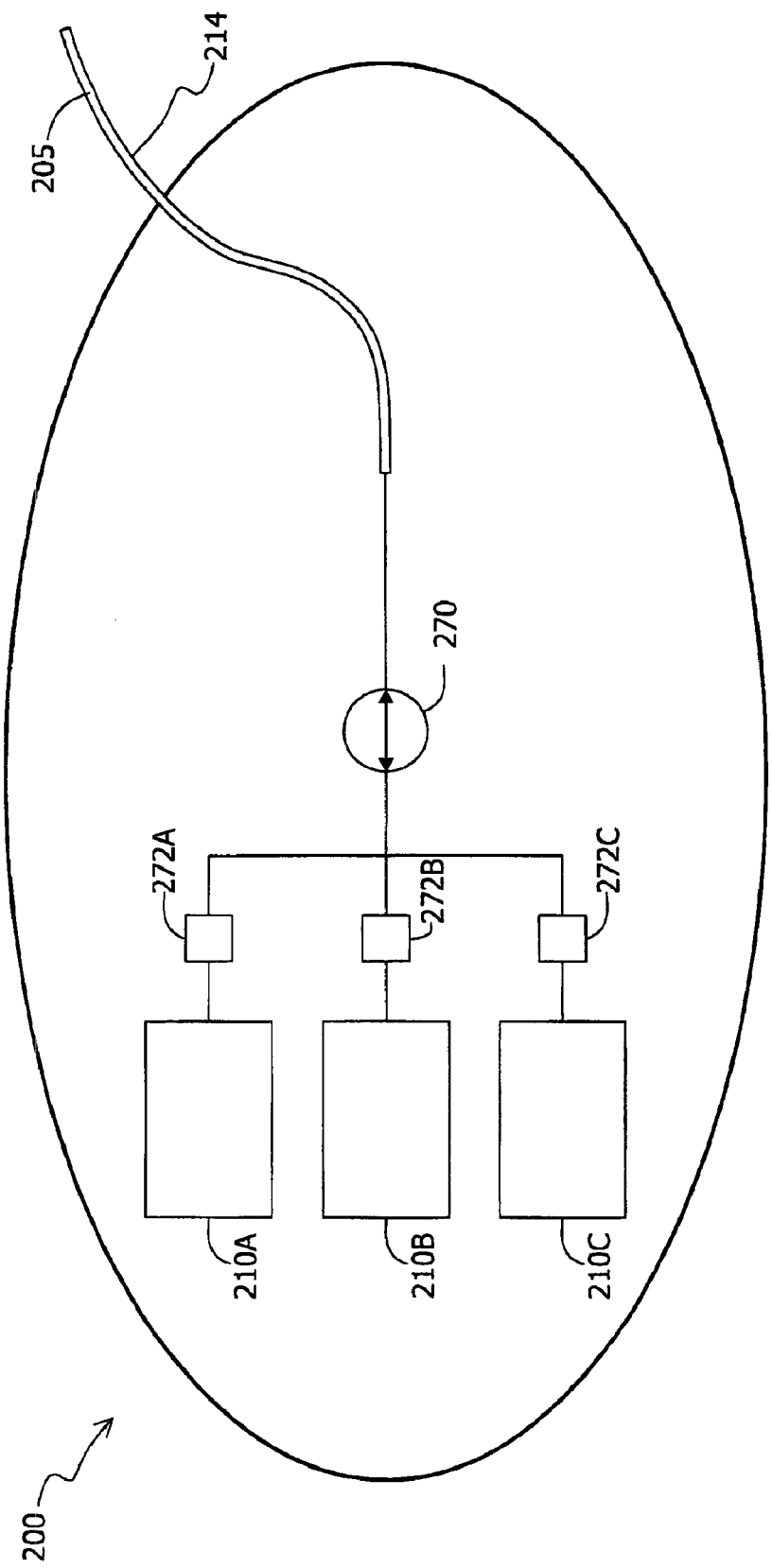
FIG. 1C is a cutaway view of a device including an extendable element and storage tanks according to an embodiment of the present invention.

FIG. 1C is a cutaway view of a device including one or more moveable elements, arms or proboscises and one or more storage tanks. For clarity, components of device 200 shown elsewhere are not shown in FIG. 1C. Referring to FIG. 1C, device 200 includes a proboscis 214 which includes a typically internal channel, lumen or hose 205. One or more tanks 210a, 210b and 210c may provide or collect fluid or other substances (e.g., medicine, bodily fluid) via tubes or pipes 274 and pump 270. In various embodiments, pump 270 may be operated to empty or fill tank(s) 210, or to both empty and fill tank(s) 210, as the application requires. Valves 272a, 272b and 272c may be provided to open, close, and control the flow to/from, the tank(s) 210. Proboscis 214 may be connected to, inter alia, the pump 270. Pump 270, valves 272a, 272b and 272c, and other components typically operate under the control of a controller such as controller 212 (FIG. 1B).

Figure 2A:
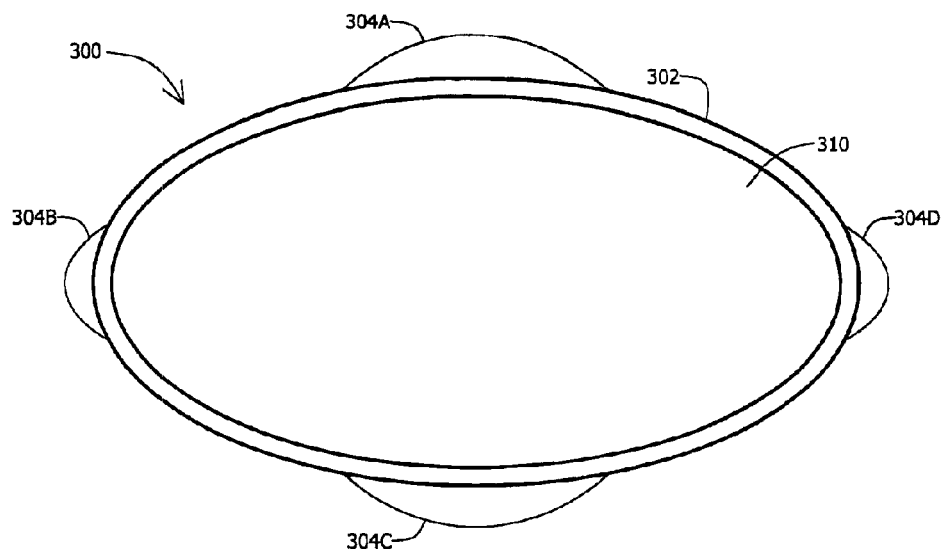
FIG. 2A is a front cross sectional view of an extendable element, in accordance with an embodiment of the present invention.
Figure 2B:
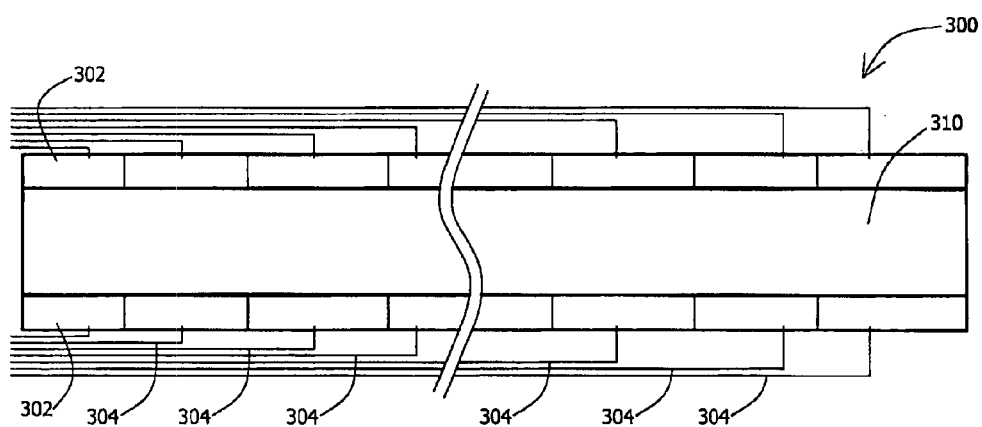
FIG. 2B is a side-sectional view of an extendable element, in accordance with an embodiment of the present invention.

Reference is made now to FIG. 2A, which is front view of a moveable element, arm or proboscis, in accordance with an embodiment of the present invention; and in addition reference is also made to FIG. 2B, which is a side-sectional view of a moveable element, arm or proboscis, in accordance with an embodiment of the present invention. As discussed above, embodiments of the proboscis 300 may be attached to or included within an in-vivo device, such as devices 100 or 200. Embodiments of the proboscis 300 may be used with other devices, such as devices having non-medical applications. The proboscis 300 may include a proboscis body 302. The proboscis 300 may further include any other suitable elements. For example the proboscis 300 may include control elements such as wires 304 (specified as 304A, 304B, 304C, and 304D in FIG. 2A, but not specified for clarity in FIG. 2B), a flexible sleeve, coatings, etc. Proboscis 300 may include, for example, a lumen or inner cavity 310. While wires and other components are shown having a certain shape, configuration, position, and number, other suitable shapes, configurations, positions, and numbers may be used. For example, wires 304A, 304B, 304C, and 304D may be substantially circular in cross section, may be flat or ribbon like, etc.

The proboscis body 302 may be designed in accordance with or to be integrated with in-vivo medical instruments, including but not limited to graspers, blades, clamps, tissue collecting baskets, scalpels, stents, catheters, suturing devices, forceps, dilatation balloons, injectors, forceps, anchors, drug applicators, samplers, biopsy samplers, an electrode or electrodes, suction tubes, temperature sensors, optical sensors, pH meters, and others.

For example, a proboscis 300 may be designed to mimic or perform the functionality of a scalpel. Such a scalpel proboscis moveable element, or arm may have a sharp edge at, for example, its distal end, suitable for cutting tissue. Another embodiment of a proboscis 300 may include an injector. The injector proboscis may be substantially hollow, such that the proboscis may be suitable for injecting material into a site of interest. Accordingly, the proboscis 300, either individually or cooperatively with additional one or more proboscis 300 or other instruments, may be adapted to perform any one or more of a variety of functions.

According to some embodiments of the present invention the proboscis body 302 may be a flexible, elastic or non-elastic, elongated solid rod or hollow tube. The specific design and the properties of each proboscis body 302 may be selected to best suite the intended purpose or function of the proboscis 300. It should be noted however, that a proboscis having a specific design may be suitable for carrying out one or more functions, or for performing more than one procedures. For example, an injector proboscis may also be suitable for taking samples of body fluids such as, for example, blood or GI tract fluids. Proboscis 300 is typically biocompatible, and may for example, be made of biocompatible material, such as, silicon or a suitable polymer or plastic. According to some embodiments of the present invention, at least a portion or portions of the proboscis body 302 may include a movement device or actuator such as a piezo material. For example the proboscis body 302 may include a plastic piezo material, such as Poly Vinlidine Fluoride (PVDF). Other movement devices, motors or actuators may be used. According to other embodiments of the present invention, at least a portion or portions of the proboscis body 302 may include shape memory material. For example the proboscis body 302 may include a Nickel Titanium alloy (NiTi), also known as NiTinol. A discussion of methods of manipulation and control of the proboscis body 302 of these and other embodiments of the present is included herein. Other movement methods may be used with embodiments of the present invention; for example those described in published U.S. application 2003/0069474 to Courvillon, Jr.

According to some embodiments of the present invention the proboscis 300 may further include one or more control wires or conductors such as wires 304. While four wires are depicted in FIGS. 2A and 2B, other suitable numbers of wires may be used. The wires 304 may be embedded into the proboscis body 302. Alternatively, the wires may be coupled (e.g. using any suitable adhesive, or by mechanical methods, or other suitable methods) to the outer surface of the proboscis body 302. The wires may be mounted at different spots; for example within the proboscis body 302 or within material forming the proboscis 300. Optionally, the wires 304 may be positioned along two or four orthogonal axis. The wires may be conductive wires capable of conducting energy to the proboscis body 302. According to one embodiment, the wires 304 may be adapted to conduct electricity. According to another embodiment, the wires 304 may be heat conductive. In other embodiments of the present invention, the wires may be omitted altogether; for example, the proboscis body itself may be piezo conductive. The wires may be operatively connected to one or more portions of the proboscis body 302. According to some embodiments the proboscis body 302 may be segmented or partially segmented and one or more wires may be operatively connected to each one of the segments of the proboscis body 302. For example, a set (where set may include one) of wires or conductors may be connected to each segment. A set of wires may traverse the proboscis starting at a proximal end, and at each segment, a suitable set of wires may attach or connect electrically to the segment, or to a portion of the segment that is a movement device or actuator; such electrically connected wires typically do not continue their traverse towards the distal end. According to some embodiments of the present invention a set of two conductive wires 304 may be coupled to each segment of the proboscis body along an orthogonal axis. According to another embodiment of the present invention a set of four conductive wires 304 may be coupled to each segment of the proboscis body 302 along an orthogonal axis.

In one embodiment, the set of control wires may include subsets of control wires, each subset being attached to each segment in a set of segments (wherein set and subset each can include one item). Movement may be controlled in more than one direction (such multi-directional movement need not be controlled by wires). For example, a subset of the control wires (for example various wires in each subset being attached to different segments or portions of the arm or extendible element) may control movement in a first direction, and wherein a subset of the control wires control movement in a second direction. For example, the first direction may be an X direction and the second direction may be a Y direction.

Referring to FIG. 2A, wires 304A, 304B, 304C, and 304D are embedded at generally 90 degree intervals around a segment of proboscis body 302. Typically, the cross section of the proboscis body 302 is elliptical, but may have other shapes. Wires 304A and 304C may be considered to be "tilt" or "vtilt" control wires and wires 304B and 304D may be considered to be "pan" or "vpan" control wires, however, these labels may be reversed if the viewer's reference is different. Other numbers of control wires per section may be used, and other numbers of possible control directions may be used. The voltage sent along the wires 304 is typically under 20 volts, and the current is typically in the microampere range, although other current levels may be used. Each of wires 304A, 304B, 304C, and 304D may attach or connect electrically to a segment, or to a portion of the segment that is a movement device or actuator.

Numerous operational protocols or methods may be used for the operation and control of a proboscis 300. The protocols may take into consideration some or all of the characteristics of the proboscis 300 and its operation and application. For example, the following characteristics of the proboscis 300 may be considered: the type of proboscis body 302, the length of the segments, the type of wires 304, the energy used, the inclusion of shape memory material in proboscis body 302, the inclusion of piezo material in the proboscis body 302 and/or other characteristics. The protocol may determine one or more of parameters of operation of the proboscis 300. For example the protocol may determine the following operation parameters: the amount of energy to be applied, the duration of each period of energy application, the polarity of the energy (e.g. when the energy is electricity) the vector of the force to be applied, which segments are to be energized, the desired level of deformation. Other parameters may also be included. For example, in case the proboscis body 302 includes shape memory material, it may be necessary to continue energizing the deformed segments in order to maintain the deformation of those segments. The parameters may be processed and an operation protocol may be devised. The operation protocol may be included in or effective by a controller. For example, controller 212, transceiver 206, controller 124 or an external controller may create appropriate signals or control commands to be sent to wires or other signal transmission devices attached to a proboscis, which may cause various segments or movement control devices on the proboscis to move appropriately. The controller may be adapted to control and to interface the operation of the proboscis 300 in accordance with the operation protocol. Accordingly, a proboscis 300 may be for example omni-directionally directed or controlled.

According to some embodiments of the present invention an electrical current may be applied to one or more wires 304 connected to one or more segments of a proboscis body 302 including, for example, PVDF, or other suitable material thereby causing those segments to deform or bend.

According to other embodiments of the present invention heat may be applied to one or more segments of a proboscis body 302 including, for example, NiTinol or other suitable material through heat conducting wires 304 embedded therein, thereby causing those segments to deform or bend.

According to further embodiments of the present invention, physical forces may be applied either directly or indirectly to segments of a flexible proboscis body 302 using for example, motors including, but not limited to mechanical, electrical, magnetic or chemical motors, and any combination thereof, thereby causing the proboscis body to deform or bend. The forces may be applied to, for example, one or more wires 304 connected to one or more segments of the proboscis body 302 and the wires may pull one or more segments of the proboscis body, thereby causing those segments to bend or deform.

Figure 3:
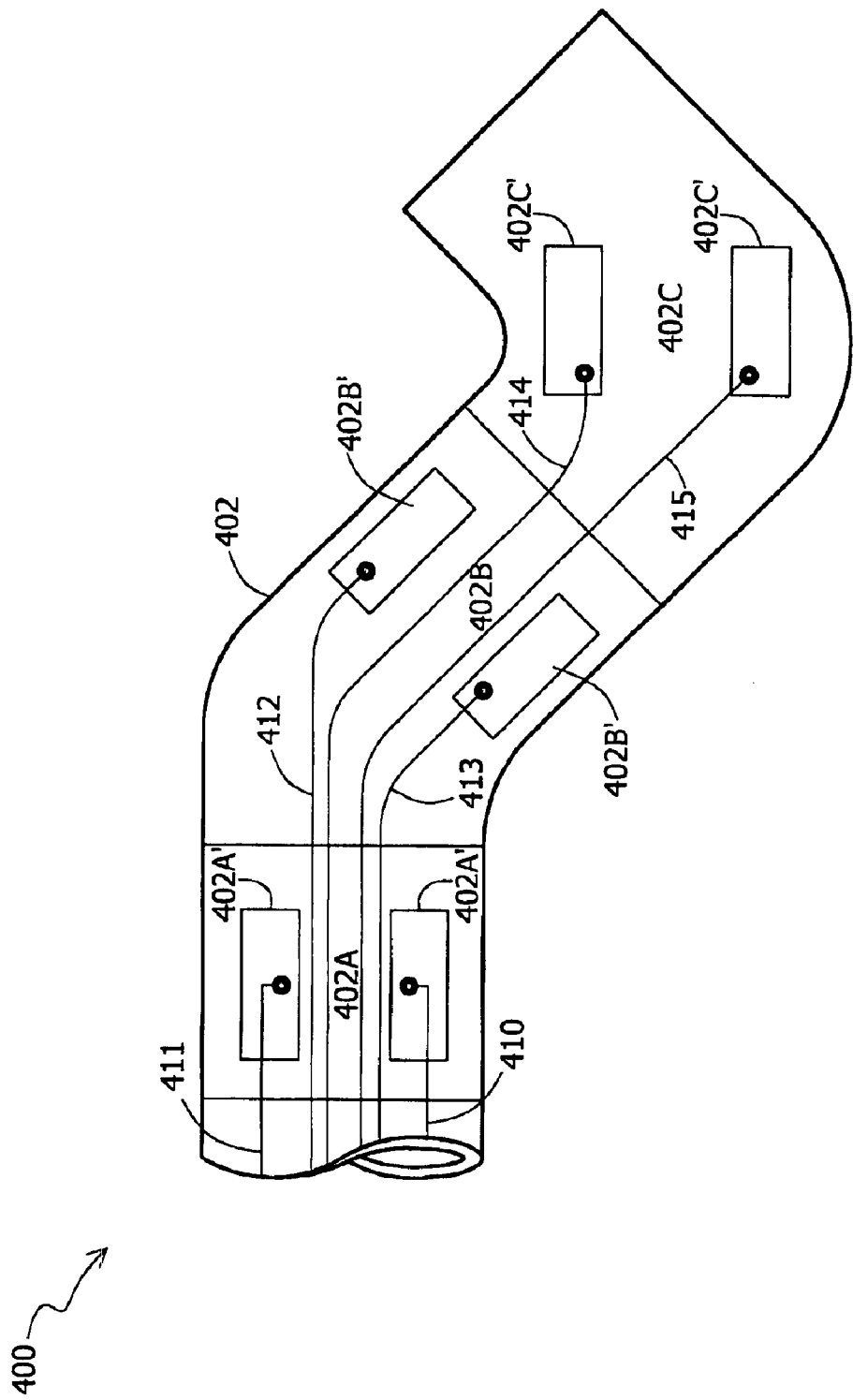
FIG. 3 illustrates a side cutaway view of a portion of an extendable element according to an embodiment of the present invention.

Reference is made now to FIG. 3, which is a side-sectional view (with a cut-away section) of a proboscis, arm, or moveable element operated in accordance with an embodiment of the present invention. In proboscis 400 the distal portion of the proboscis body 402 may be segmented into, for example, three autonomous segments 402A, 402B, 402C. Other numbers of segments may be used. Each of the segments 402A, 402B and 402C may include one or more movement device or actuators, for example, piezo material areas or sections 402A', 402B' and 402C', including material such as PVDF, that, for example, may be preprogrammed or manufactured to undergo conformational changes when an electrical current is applied to the material. For example the piezo material such as piezo material areas or sections 402A', 402B' and 402C' may be programmed to increasingly deform from a pre-programmed configuration (e.g., coiled, straight, bent or other shape) in response to an increase in the current level applied thereto. Alternately, piezo material may be programmed to deform in one direction when applied with a first current, and deform in an opposite direction when applied with a second current having an inverse polarity. Electricity conductive wires 410, 411, 412, 413, 414 and 415 may be embedded into or attached to segments 402A, 402B and 402C and embedded into attached to a movement device, region or actuator such as piezo material areas or sections 402', 402B' and 402C'. Wires 410, 411, 412, 413, 414 and 415 may be embedded or attached at one or suitable more points or continuously for each section; in FIG. 3 wires are connected at one point each. In the embodiment shown a pair of wires 410, 411, 412, 413, 414 and 415 may be embedded opposite to each other in each of the segments 402A, 402B and 402C.

A first voltage may be applied by wire 414 and/or 415 to segment 402C, thereby causing all or a portion of the piezo material 402C' to react and segment 402C to deform upwards. A second voltage may be applied by wire 412 and/or 413 to segment 402B, thereby causing all or part of piezo material 402B' to react and segment 402B to deform downwards. Typically, the amount of deformation depends on the amount of voltage and current and, typically, the current is a constant DC current, although other currents may be used. According to some embodiments of the present invention, each of the segments 402A, 402B and 402C may return to its original form (e.g., straight, coiled) when it is no longer energized, thus it may be necessary to maintain the currents for as long as deformation of the corresponding segments 402 is required. The voltages or currents may be adjusted to deform the segments 402A, 402B and 402C in different directions or angles. In a typical embodiment, additional wires and movement device or actuators (not shown) may be embedded to move the segments 402 at an angle perpendicular to the angle shown.

Figure 4:
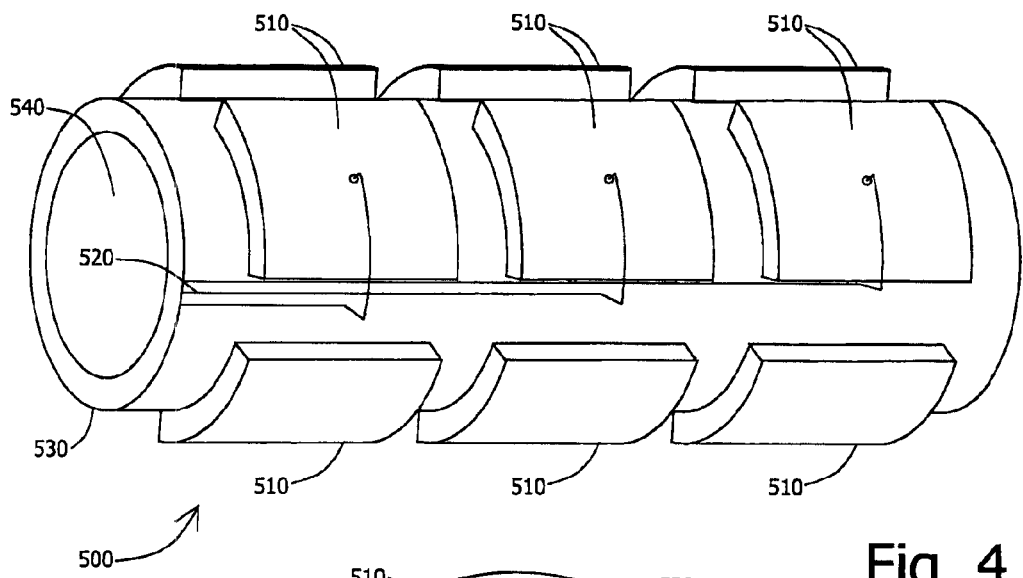
FIG. 4 illustrates a cutaway view of a portion of an extendable element, according to one embodiment of the present invention.
Figure 5:
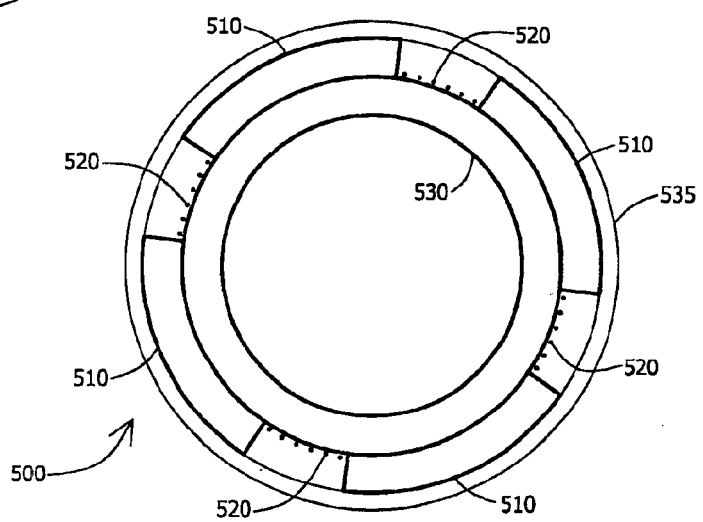
FIG. 5 illustrates a cross sectional view of the extendable element of FIG. 4, according to one embodiment of the present invention.

FIG. 4 depicts an alternate structure for an extendable element according to an embodiment of the present invention. FIG. 5 illustrates a cross sectional view of the extendable element of FIG. 4, according to an embodiment of the invention. Referring to FIG. 4 and FIG. 5, arm, proboscis or extendable element 500 includes movement devices, regions or actuators such as piezo elements 510 controlled by electric current delivered by conductors 520. The extendable element 500 may include an inner shell 530, an outer shell 535 (not depicted in FIG. 4 for the sake of clarity), and possibly a lumen or inner space 540. The inner shell 530 and outer shell 535 may be non-conductive, insulating, and may protect the piezo elements 510 from, for example, external body fluids or from substances flowing within the lumen 540. The inner shell 530 and outer shell 535 may be flexible, but rigid enough to keep a certain shape when piezo elements 510 are not active.

When current is applied via conductors 520 to piezo elements 510, extendable element 500 may move in a controlled manner. The extendable element 500 may be stored as, for example, a spiral or coil. The extendable element 500 may be pre-stressed so that, when no current is applied, it is shaped as a spiral or coil. In one embodiment, piezo element is a tube approximately 1 mm in diameter, approximately 15–20 mm in length, and may be stored as a spiral having an average diameter of approximately 3 mm. In one embodiment, about 200 sets of four piezo elements are used (each piezo element spaced at a 90 degree interval around the extendable element, as depicted in FIG. 5), and each piezo element-typically extends approximately 100 microns along the length of the extendable element and provides approximately 5 degrees of curvature, when fully activated. Different dimensions and different numbers of piezo elements or other suitable movement devices, regions or actuators may be used.

Figure 6:
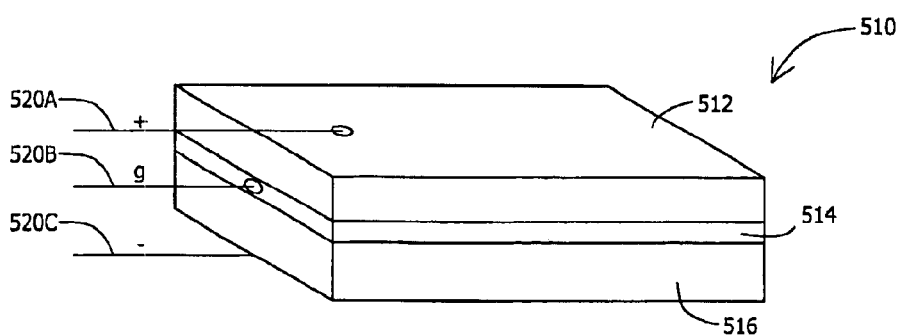
FIG. 6 illustrates a piezo element of the extendable element of FIG. 4, according to one embodiment of the present invention.

FIG. 6 illustrates a piezo element of the extendable element of FIG. 4, according to an embodiment of the invention. Other suitable piezo elements, having other suitable structures may be used, and other suitable movement devices, regions or actuators may be used. Referring to FIG. 6, piezo element 510 may include a first piezo material 512, an inner conductive layer 514 (which may include, for example, metal foil, conductive polymer, or other suitable material), and a second piezo material 514. Positive conductor 520A may be connected to first piezo material 512, negative conductor 520C may be connected to second piezo material 516, and central conductor 520B may be connected to inner conductive layer 514, to provide a circuit for conductors 520A and 520C.

In operation, when positive voltage is applied to positive conductor 520A and first piezo material 512, the first piezo material 512 expands. When negative voltage is applied to negative conductor 520C and second piezo material 512, the second piezo material 512 contracts. As a result of current being applied to conductors 520A and 520C, the piezo element 510 bends, creating a radius of curvature. This operation may be similar to an operation which is described in, for example, "Electroactive Polymer Actuators as Artificial Muscles," Y. Bar-Cohen, Ed., Spie Press, 2001, incorporated herein by reference in its entirety.

The conductors 520 are typically connected to a controller, such as discussed elsewhere herein. By proper activation of certain piezo elements 510, the shape and motion of the extendable element 500 may be controlled.

In alternate embodiments other numbers and arrangements of piezo elements and control elements may be used. Other structures may be used; for example, inner and outer shell elements need not be used or may be of different construction, and the extendable element may have a different cross section (e.g., oval, substantially rectangular, etc.).

Figure 7:
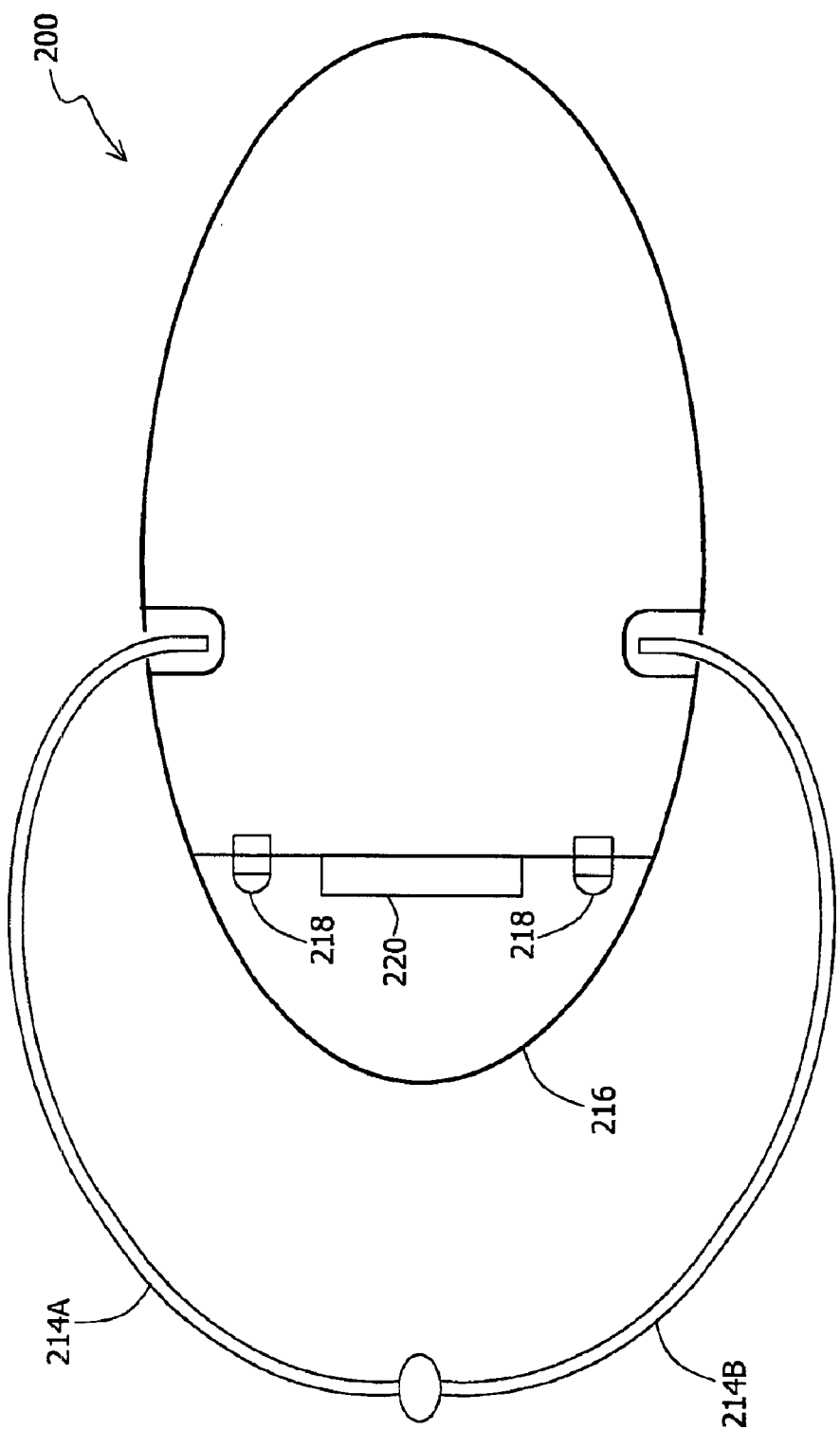
FIG. 7 illustrates a capsule with multiple extendable elements according to an embodiment of the present invention.

Referring to FIG. 7, there is shown a device such as a capsule with two proboscises. Device 200 includes a dome or cover 216, an imager 220, and one or more illumination devices 218. The proboscises 214A and 214B may, for example, manipulate objects in the filed of view of the imager.

Device 200 may achieve greater maneuverability and control by, for example, using one or more proboscis arms to move, hold or propel the device 200, for example, by pushing the device against lumen walls or other structures, grasping lumen walls or other structures, or by propelling the device in fluid. The proboscises may, for example, act as an arm to perform a variety of tasks and/or may be used as a leg to propel the device; as discussed above tools or other devices may be attached to or part of the proboscis. Graspers may be included at the end of such proboscises to aid motility.

Those with ordinary skill in the art may appreciate that other embodiments of the present invention may enable a controlled omni-directional deformation of the proboscis. It may thus be possible to attach an instrument or sensor, for example an image sensor, to the tip of the proboscis body, and the proboscis can be deflected, for example, to enable a view of lateral and rear areas.

It will be appreciated by those skilled in the art that while the invention has been described with respect to a limited number or embodiments, many variations, modifications and other applications of the invention may be made which are within the scope and spirit of the invention.

What is claimed is:

1. An autonomous in-vivo device comprising:
   a housing; and
   a moveable arm;
   said housing configured to store the moveable arm and said movable arm configured to be coiled when stored within the housing.

2. The device of claim 1, comprising an imager.

3. The device of claim 1, comprising a transmitter.

4. The device of claim 3, wherein the transmitter is to transmit via radio waves.

5. The device of claim 1, wherein the moveable arm is hollow.

6. The device of claim 1, wherein the moveable arm includes a tube.

7. The device of claim 1, wherein the moveable arm includes a plurality of segments.

8. The device of claim 1, comprising a set of control wires.

9. The device of claim 1, wherein the moveable arm includes a movement device.

10. The device of claim 1, wherein the moveable arm includes a piezo material.

11. The device of claim 1, wherein the moveable arm includes a shape memory material.

12. The device of claim 1, comprising a controller to send movement signals to the moveable arm.

13. The device of claim 1, comprising a storage tank.

14. An in-vivo device comprising:

a housing;

a transmitter; and a moveable proboscis;

said housing configured to store the movable proboscis and said movable proboscis configured to be coiled when stored within the housing.

15. The device of claim 14, comprising an imager.

16. The device of claim 14, wherein the transmitter is to transmit via radio waves.

17. The device of claim 14, wherein the proboscis includes a tube.

18. The device of claim 14, wherein the proboscis includes piezo material segments.

19. An in-vivo device comprising:

a housing;

a moveable means to manipulate a structure in-vivo;

said housing configured to store the movable means and said movable means configured to be coiled when stored within the housing.

20. The in-vivo device of claim 19, comprising an imaging means to capture images.

21. The in-vivo device of claim 19, comprising a transmitter means to transmit images.

22. An autonomous in-vivo device comprising:

a housing;

an imager; and an arm extending from the device, the arm comprising a plurality of segments;

said housing configured to store the arm extending from the device and said arm extending from the device configured to be coiled when stored within the housing.

23. The device of claim 22 comprising a set of control wires, a subset of the control wires being attached to each of a set of segments.

24. The device of claim 23 wherein a subset of the control wires control movement in a first direction, and wherein a subset of the control wires control movement in a second direction.

25. The device of claim 22, comprising a radio transmitter.

26. An autonomous in-vivo device comprising:

a housing;

an imager;

an arm extending from the device, the arm comprising a plurality of segments and being controllable;

said housing configured to store the arm and said arm configured to be coiled when stored within the housing.

* * * * *